United States Patent
Kariniemi et al.

(10) Patent No.: US 10,201,336 B2
(45) Date of Patent: Feb. 12, 2019

(54) DEVICE AND METHOD FOR DELIVERING A VASCULAR DEVICE

(75) Inventors: Ryan Douglas Kariniemi, Cokato, MN (US); Mathias C. Glimsdale, St. Michael, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 883 days.

(21) Appl. No.: 13/072,378

(22) Filed: Mar. 25, 2011

(65) Prior Publication Data
US 2012/0245668 A1  Sep. 27, 2012

(51) Int. Cl.
*A61B 17/00* (2006.01)

(52) U.S. Cl.
CPC ... *A61B 17/0057* (2013.01); *A61B 2017/00575* (2013.01); *A61B 2017/00592* (2013.01);
(Continued)

(58) Field of Classification Search
CPC ........... A61B 17/0057; A61B 17/12; A61B 17/12022–17/12045; A61B 17/12099–17/12122; A61B 17/12131–17/12195; A61B 17/1204; A61B 17/1214; A61B 17/1215; A61B 2017/00575–2017/00632; A61B 2017/00641–2017/00659; A61B 2017/00676; A61B 2017/12004;
(Continued)

(56) References Cited

U.S. PATENT DOCUMENTS

| 4,991,602 A | 2/1991 | Amplatz et al. |
| 5,067,489 A | 11/1991 | Lind |

(Continued)

FOREIGN PATENT DOCUMENTS

| CN | 1394132 | 1/2003 |
| CN | 101234034 | 8/2008 |

(Continued)

OTHER PUBLICATIONS

International Search Report and Written Opinion from International Application No. PCT/US2012/028266, dated Jul. 5, 2012.
(Continued)

*Primary Examiner* — Ryan J Severson
*Assistant Examiner* — Christian Knauss
(74) *Attorney, Agent, or Firm* — Armstrong Teasdale LLP

(57) ABSTRACT

A device and method for delivering a vascular device to a target site is provided that allows an orientation of the vascular device at the target site to be adjusted by a user. In general, the delivery device includes an outer tubular member, an intermediate tubular member within the outer tubular member, and an inner member that can move axially within the intermediate tubular member. Each of the members defines a proximal end and a distal end. The intermediate and outer tubular members are fixed at their respective proximal ends, but are not fixed at their distal ends. Thus, a torque applied to the proximal end of the intermediate tubular member is at least partially transmitted to the distal end of the intermediate tubular member, allowing the user to rotate an attached vascular device by rotating the proximal end of the intermediate tubular member.

31 Claims, 15 Drawing Sheets

(52) U.S. Cl.
CPC .............. *A61B 2017/00606* (2013.01); *A61B 2017/00623* (2013.01)

(58) Field of Classification Search
CPC ............. A61B 2017/1205–2017/12095; A61B 2017/12127; A61F 2002/011; A61F 2002/9505; A61F 2002/9511; A61F 2002/9522; A61F 2002/9528; A61F 2002/9534; A61F 2/95; A61F 2/954; A61M 25/00; A61M 25/0014; A61M 25/0021; A61M 25/0023; A61M 25/0041; A61M 25/0043; A61M 25/0071; A61M 25/0097; A61M 25/01; A61M 25/0172; A61M 2025/0004; A61M 2025/0006; A61M 2025/0034; A61M 2025/0035; A61M 2025/0036; A61M 2025/0039; A61M 2025/004; A61M 2025/0042; A61M 2025/0098; A61M 2025/0175; A61M 2025/0177

See application file for complete search history.

(56) References Cited

U.S. PATENT DOCUMENTS

| | | | |
|---|---|---|---|
| 5,108,420 A | 4/1992 | Marks | |
| 5,192,301 A | 3/1993 | Kamiya et al. | |
| 5,725,546 A * | 3/1998 | Samson | A61B 17/12022 606/191 |
| 5,725,552 A | 3/1998 | Kotula et al. | |
| 5,846,261 A | 12/1998 | Kotula et al. | |
| 5,895,391 A * | 4/1999 | Farnholtz | A61B 17/12022 606/108 |
| 5,944,738 A | 8/1999 | Amplatz et al. | |
| 5,976,174 A | 11/1999 | Ruiz | |
| 6,077,291 A | 6/2000 | Das | |
| 6,123,715 A | 9/2000 | Amplatz | |
| 6,214,029 B1 | 4/2001 | Thill et al. | |
| 6,334,864 B1 | 1/2002 | Amplatz et al. | |
| 6,368,339 B1 | 4/2002 | Amplatz | |
| 6,402,772 B1 * | 6/2002 | Amplatz et al. | 606/200 |
| 6,447,531 B1 | 9/2002 | Amplatz | |
| 6,551,344 B2 | 4/2003 | Thill | |
| 6,579,303 B2 | 6/2003 | Amplatz | |
| 6,911,037 B2 | 6/2005 | Gainor et al. | |
| 7,041,125 B2 * | 5/2006 | Hwang et al. | 623/1.11 |
| 7,144,410 B2 | 12/2006 | Marino et al. | |
| 7,288,105 B2 | 10/2007 | Oman et al. | |
| 8,114,144 B2 | 2/2012 | Chow | |
| 8,313,505 B2 | 11/2012 | Amplatz et al. | |
| 2001/0003801 A1 | 6/2001 | Strecker | |
| 2002/0183787 A1 * | 12/2002 | Wahr | A61B 17/0057 606/213 |
| 2002/0198563 A1 | 12/2002 | Gainor et al. | |
| 2003/0055455 A1 | 3/2003 | Yang et al. | |
| 2003/0139819 A1 | 7/2003 | Beer et al. | |
| 2003/0233140 A1 * | 12/2003 | Hartley et al. | 623/1.11 |
| 2004/0002727 A1 | 1/2004 | Hwang | |
| 2004/0236403 A1 * | 11/2004 | Leonhardt et al. | 623/1.13 |
| 2005/0021057 A1 | 1/2005 | Goar | |
| 2005/0060018 A1 * | 3/2005 | Dittman | 623/1.11 |
| 2005/0228434 A1 | 10/2005 | Amplatz et al. | |
| 2005/0267523 A1 * | 12/2005 | Devellian et al. | 606/213 |
| 2006/0122647 A1 * | 6/2006 | Callaghan et al. | 606/213 |
| 2006/0135961 A1 * | 6/2006 | Rosenman | A61M 25/0045 606/108 |
| 2006/0241690 A1 | 10/2006 | Amplatz et al. | |
| 2007/0066993 A1 * | 3/2007 | Kreidler | 606/213 |
| 2007/0118207 A1 * | 5/2007 | Amplatz et al. | 623/1.12 |
| 2007/0123927 A1 | 5/2007 | Farnan | |
| 2007/0233171 A1 | 10/2007 | Gilson | |
| 2007/0265656 A1 | 11/2007 | Amplatz et al. | |
| 2008/0033475 A1 | 2/2008 | Meng | |
| 2008/0200945 A1 | 8/2008 | Amplatz et al. | |
| 2008/0215008 A1 * | 9/2008 | Nance et al. | 604/164.03 |
| 2008/0221657 A1 * | 9/2008 | Laroya et al. | 623/1.12 |
| 2008/0262518 A1 | 10/2008 | Freudenthal | |
| 2009/0018562 A1 | 1/2009 | Amplatz et al. | |
| 2009/0062841 A1 | 3/2009 | Amplatz et al. | |
| 2009/0062844 A1 | 3/2009 | Tekulve et al. | |
| 2009/0157162 A1 * | 6/2009 | Chow et al. | 623/1.11 |
| 2009/0187214 A1 | 7/2009 | Amplatz et al. | |
| 2009/0264980 A1 * | 10/2009 | Mackay | 623/1.12 |
| 2010/0030200 A1 * | 2/2010 | Strauss | A61B 17/12022 606/1 |
| 2010/0121370 A1 | 5/2010 | Kariniemi | |
| 2010/0274341 A1 * | 10/2010 | Rasmussen et al. | 623/1.11 |

FOREIGN PATENT DOCUMENTS

| | | |
|---|---|---|
| CN | 101687088 A | 3/2010 |
| WO | 2008156464 A1 | 12/2008 |
| WO | WO 2009147349 A1 * | 12/2009 |

OTHER PUBLICATIONS

International Search Report and Written Opinion from International Patent Application No. PCT/US2012/028271, dated Jul. 18, 2012, 10 pages.

* cited by examiner

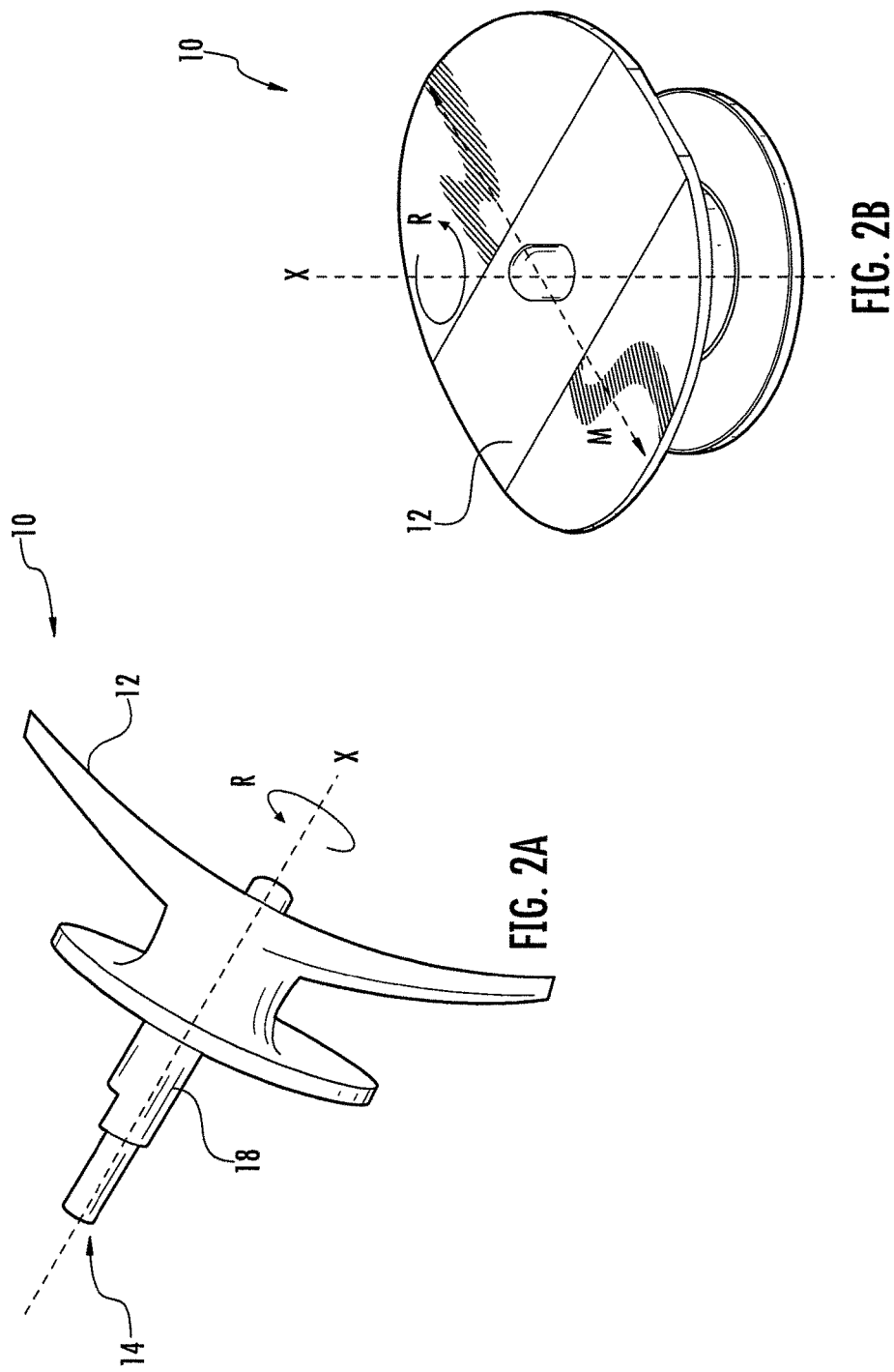

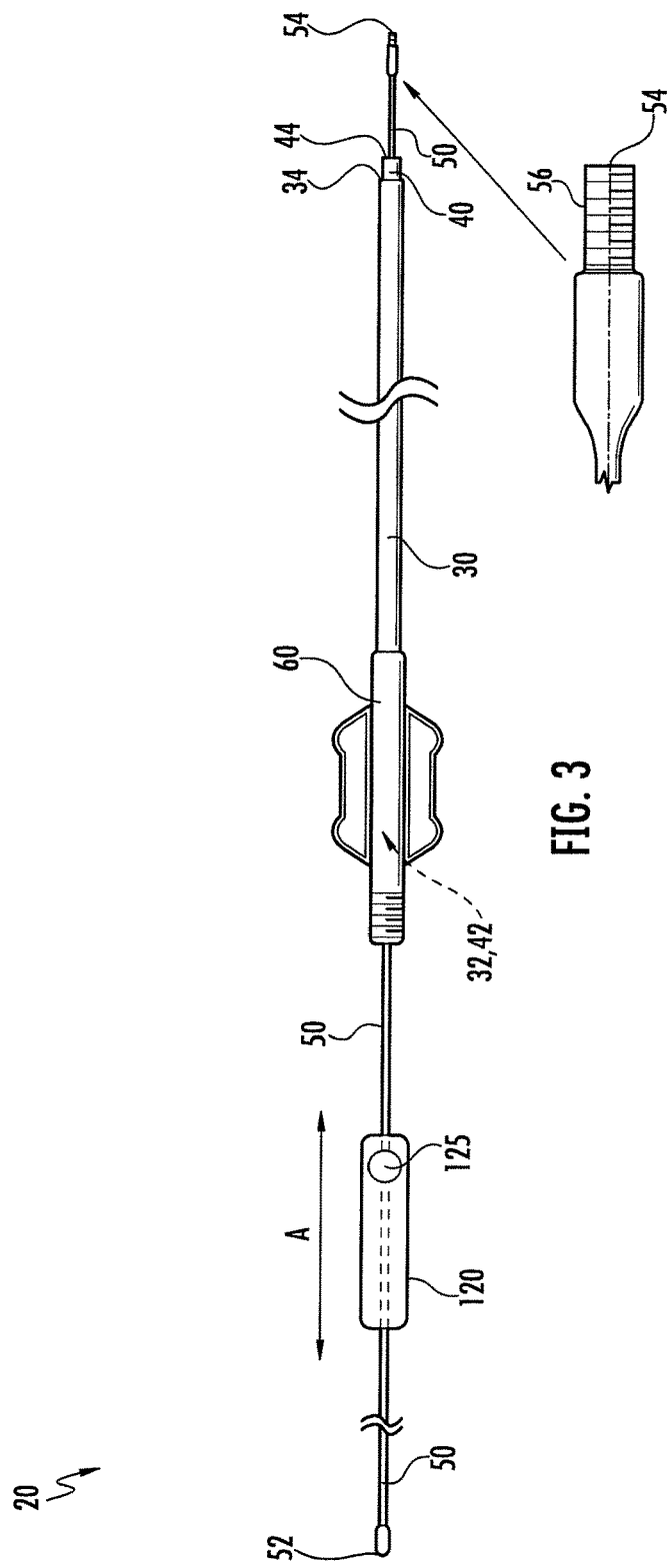

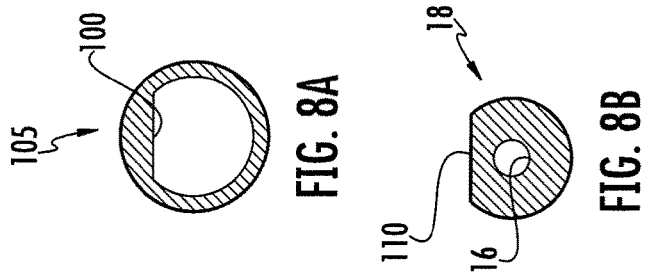
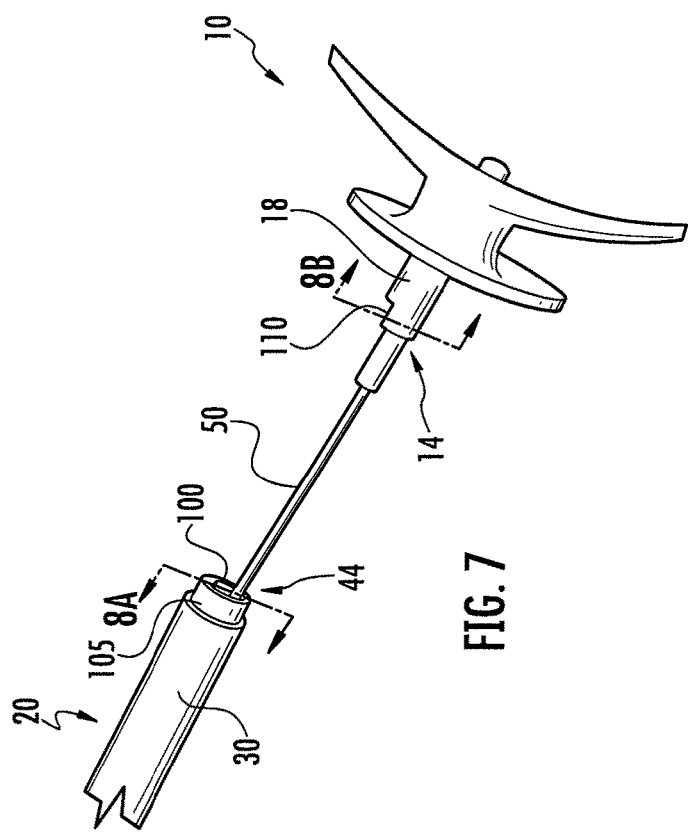

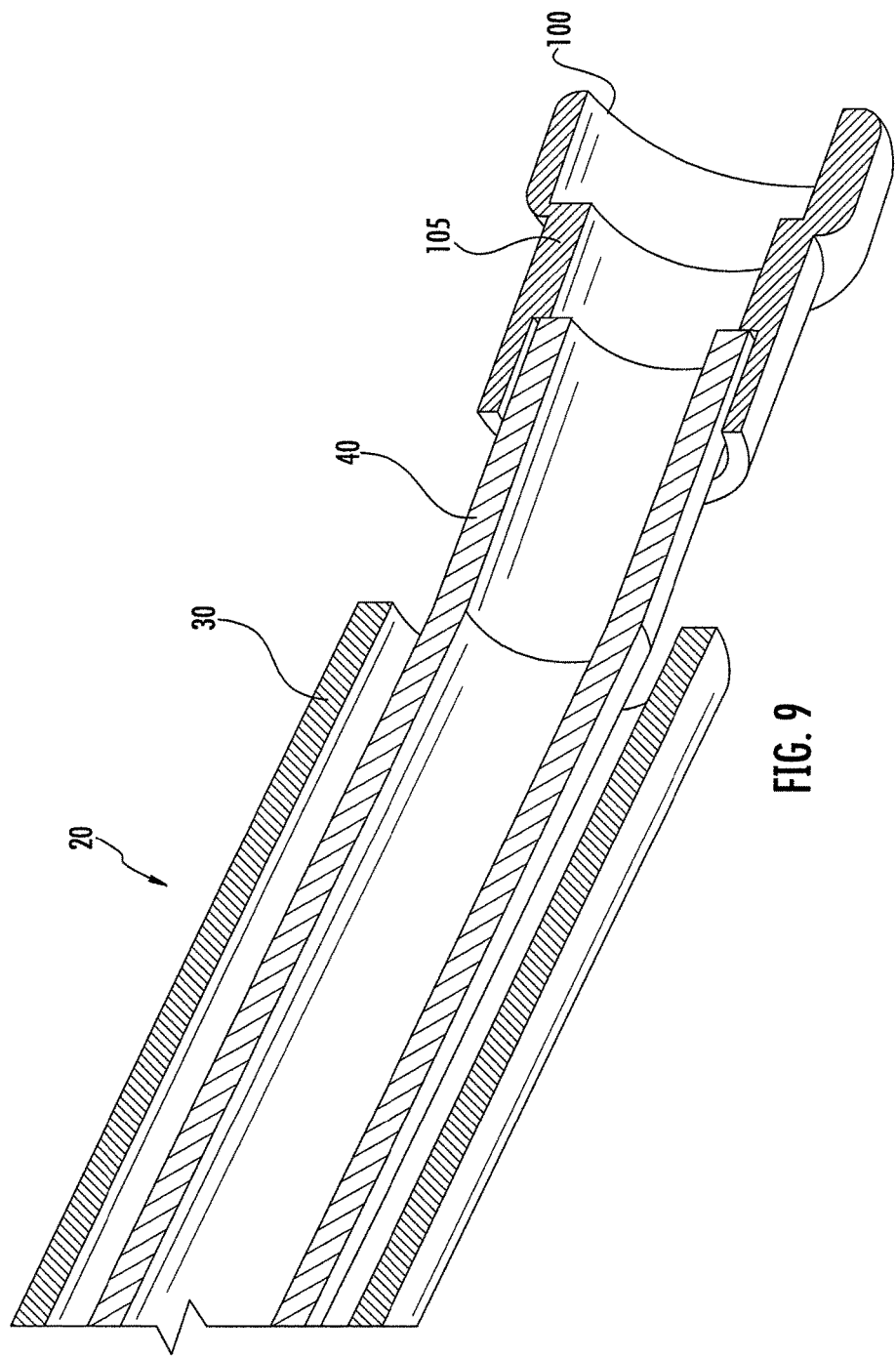

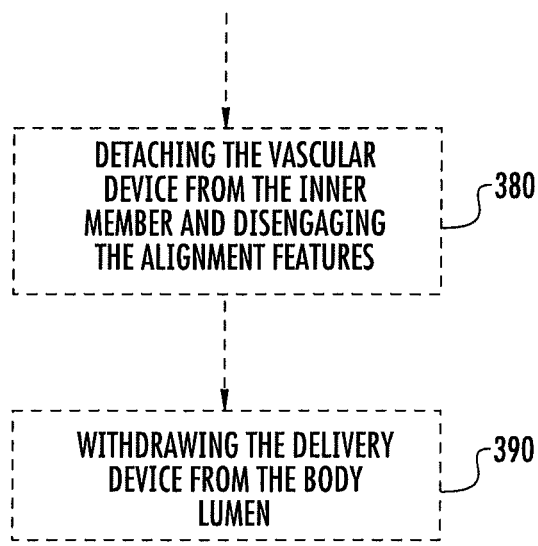

DEVICE AND METHOD FOR DELIVERING A VASCULAR DEVICE

BACKGROUND

I. Field of the Invention

Embodiments of the present invention relate generally to delivery devices for positioning and deploying vascular devices within a body lumen for treating certain medical conditions. In particular, embodiments are directed to delivery devices for positioning and deploying non-symmetric vascular devices.

II. Description of the Related Art

Over the past few decades, advances have been made in the diagnosis and treatment of septal defects, such as atrial septal defects and ventricular septal defects. In general, septal defects are congenital heart defects in which the inner wall separating the left and right sides of the heart (i.e., the septum) has a hole or an opening that has failed to close.

FIGS. 1A and 1B show schematic representations of a patient's heart 205. In FIG. 1A, the patient's heart 205 has a hole 210 in the septum 215 between the heart's two upper chambers (the left atrium 220 and the right atrium 225), called an atrial septal defect (ASD). In FIG. 1B, the patient's heart 205 has a hole 210 in the septum 215 between the heart's two lower chambers (the left ventricle 230 and the right ventricle 235), called a ventricular septal defect (VSD). Ventricular septal defects can occur in any location of the ventricular septum. Two common locations for these defects are the perimembranous septum and the muscular septum.

As a result of an atrial septal defect or a ventricular septal defect, blood is able to pass from the left side of the heart to the right side, mixing oxygen-rich blood with oxygen-poor blood. This can cause a variety of problems for the individual as time goes on, such as pulmonary hypertension, right-sided heart failure, atrial fibrillation or flutter, and stroke.

One way to non-surgically treat septal defects is to permanently place a vascular device, such as an occluding device, in the heart to cover the hole. The vascular device is typically delivered to the site of the septal defect using a delivery device, which, in conjunction with other delivery instruments, is inserted into the blood vessel in the patient's groin and passed through vessels into the heart's chambers. At the site of the defect, the vascular device may be deployed, detached from the delivery device, and left permanently placed in the hole. With time, the lining of the heart wall should grow over the vascular device to seal the hole completely.

The configuration of the particular vascular device used to repair the defect may depend on the size and location of the defect. In addition to positioning the vascular device at the correct location with respect to the defect, the vascular device may need to be rotated to achieve an appropriate orientation with respect to adjacent tissue and body structures.

Accordingly, there is a need for an improved delivery device that allows a user to easily and accurately change the orientation of a vascular device within the body lumen and is able to interface with other vascular device delivery instruments to accurately place the vascular device at the defect site.

SUMMARY OF THE INVENTION

Embodiments therefore provide a delivery device for delivering a vascular device to a target site such that an orientation of the vascular device at the target site may be adjusted by a user. In general, the delivery device includes an outer tubular member, an intermediate tubular member at least partially disposed within the outer tubular member, and an inner member at least partially disposed within the intermediate tubular member and configured to move axially within the intermediate tubular member. Each of the outer tubular member, the intermediate tubular member, and the inner member defines a proximal end and a distal end. The intermediate and outer tubular members are fixed at their respective proximal ends, but are not fixed at their distal ends. Thus, a torque applied to the proximal end of the intermediate tubular member is at least partially transmitted to the distal end of the intermediate tubular member, allowing the user to rotate an attached vascular device by rotating the proximal end of the intermediate tubular member.

In one embodiment, a device for delivering a vascular device within a body lumen is provided. The delivery device may comprise an outer tubular member defining a proximal end and a distal end and an intermediate tubular member at least partially disposed within the outer tubular member, wherein the intermediate tubular member defines a proximal end and a distal end. The device may further comprise an inner member at least partially disposed within the intermediate tubular member and configured to move axially therein. The inner member may define a proximal end and a distal end, and the distal end may be configured to engage a vascular device. The proximal end of the outer tubular member and the proximal end of the intermediate tubular member may be fixed to each other, and the distal end of the intermediate tubular member may be free to rotate with respect to the distal end of the outer tubular member. As such, a torque applied proximate the proximal end of the outer tubular member may be at least partially transmitted to the distal end of the intermediate tubular member.

In some cases, the outer tubular member may define a first length, the intermediate tubular member may define a second length, and the inner member may define a third length. The first length may be shorter than the second length and the second length may be shorter than the third length. The inner member may define threads at the distal end thereof configured to engage corresponding threads of the vascular device.

In some embodiments, the intermediate tubular member may comprise an alignment feature at the distal end thereof that is configured to engage a corresponding alignment feature of the vascular device such that a rotation of the distal end of the intermediate tubular member results in a corresponding rotation of the vascular device. The alignment feature may comprise a D-shaped coupling. The delivery device may further comprise a handle that is selectively fixed to the proximal end of the inner member, wherein the axial position of the handle along the inner member is adjustable, and wherein fixation of the handle to the inner member is configured to maintain engagement of the alignment features.

The outer tubular member may define a prebend in a distal portion thereof configured to facilitate insertion of the delivery device through the body lumen. The prebend may have a curvature of between approximately 150° and approximately 210°. In some cases, the delivery device may further comprise a hub at which the proximal end of the outer tubular member and the proximal end of the intermediate tubular member are fixed to each other. The hub may comprise at least one wing configured to facilitate alignment of the prebend with a prebend of a delivery sheath through which the delivery device is moved. The prebend may lie substantially within a first plane, and the at least one wing may define a second plane that is substantially parallel to the first plane.

In some embodiments, the intermediate tubular member may comprise a plurality of spirally wound filaments. The intermediate tubular member may comprise at least two metallic filaments spirally wound in alternating directions, and in some cases may comprise three metallic filaments spirally wound in alternating directions.

The vascular device may be a non-symmetric occluding device.

In some cases, the delivery device may be configured to be passed through a device introducer, wherein the device introducer is configured to radially constrain the vascular device from an expanded state to a contracted state. A distal end of the device introducer may be configured to be attached to a proximal end of a delivery sheath, and the vascular device and at least a distal portion of the delivery system may be configured to move axially through the delivery sheath for positioning the vascular device proximate a target site within the body lumen.

In other embodiments, a device for deploying a vascular device within a body lumen is provided. The delivery device may comprise an outer tubular member defining a proximal end and a distal end, an intermediate tubular member comprising at least a first filament and a second filament and an inner member at least partially disposed within the intermediate tubular member and configured to move axially therein. The first and second filaments may be spirally wound in alternating directions and the second filament may be wound over top of the first filament. The intermediate tubular member may be at least partially disposed within the outer tubular member and may define a proximal end and a distal end. Furthermore, the inner member may define a proximal end and a distal end, and the distal end may be configured to engage a vascular device. The proximal end of the outer tubular member and the proximal end of the intermediate tubular member may be fixed to each other, and the distal end of the intermediate tubular member may be free to rotate with respect to the distal end of the outer tubular member. A torque applied proximate the proximal end of the outer tubular member may be transmitted to the distal end of the intermediate tubular member and may serve to rotate the vascular device.

In still other embodiments, a method for orienting a vascular device within a body lumen is provided. The method may include providing a delivery device defining a proximal end and a distal end; attaching a vascular device to the distal end of the inner member; positioning the delivery device and the attached vascular device within a body lumen; and changing a rotational orientation of the vascular device by applying a torque to the proximal end of the intermediate tubular member. In this regard, the delivery device may comprise an outer tubular member defining a proximal end and a distal end. The delivery device may also comprise an intermediate tubular member at least partially disposed within the outer tubular member, wherein the intermediate tubular member defines a proximal end and a distal end, and wherein the proximal end of the outer tubular member is fixed to the proximal end of the intermediate tubular member and the distal end of the intermediate tubular member is free to rotate with respect to the distal end of the outer tubular member. Furthermore, the delivery device may include an inner member at least partially disposed within the intermediate tubular member and configured to move axially therein, wherein the inner member defines a proximal end and a distal end.

In some cases, the method may further include attaching a device introducer to the distal end of the delivery device and proximally retracting the inner member with respect to the device introducer to constrain the vascular device to a contracted state within the device introducer. A delivery sheath may be attached to a distal end of the device introducer to facilitate positioning of the delivery device within the body lumen. The delivery device and the vascular device may be advanced through the device introducer and the delivery sheath to radially constrain the vascular device from the contracted state to an expanded state proximate a target site. In some cases, the method may include at least partially recapturing the vascular device within the delivery sheath. An alignment feature disposed at the distal end of the intermediate tubular member may be engaged with a corresponding alignment feature of the vascular device. In some cases, this may involve axially retracting the inner member in a proximal direction with respect to the intermediate tubular member. In addition, the alignment features may be fixed in an engaged position such that axial movement of the inner member with respect to the intermediate member is prevented.

In some cases, the method further includes detaching the vascular device from the distal end of the inner member and disengaging the alignment feature of the intermediate tubular member from the corresponding alignment feature of the vascular device. The vascular device may be detached from the distal end of the inner member, and the delivery device may be withdrawn from the body lumen.

In some embodiments, the outer tubular member may include a prebend, and the method may further comprise the step of verifying an alignment of the prebend with respect to a prebend of a delivery sheath through which the delivery device is passed. In addition, the step of changing the rotational orientation of the vascular device may comprise applying a torque to the proximal end of the intermediate tubular member to rotate the distal end of the intermediate tubular member without rotating the distal end of the outer tubular member.

BRIEF DESCRIPTION OF THE DRAWINGS

The foregoing features and advantages of embodiments of the invention will become apparent to those skilled in the art from the following detailed description of a preferred embodiment, especially when considered in conjunction with the accompanying drawings in which like numerals in the several views refer to corresponding parts.

FIG. 2A is a side view illustration of a vascular device in an expanded state according to an exemplary embodiment;

FIG. 2B is a perspective illustration of a vascular device in an expanded state according to an exemplary embodiment;

FIG. 3 is a schematic illustration of a delivery device according to an exemplary embodiment;

FIG. 7 is an illustration of a delivery device that is engaged with a vascular device according to an exemplary embodiment;

FIG. 8A is a detail view of an alignment feature of the delivery device of FIG. 7;

FIG. 8B is a detail view of a corresponding alignment feature of the vascular device of FIG. 7;

FIG. 9 is a perspective cross-sectional view of a distal end of the delivery device of FIG. 7 according to an exemplary embodiment;

FIG. 11A-11D illustrates a flowchart of a method of delivering a vascular device according to an exemplary embodiment.

DETAILED DESCRIPTION

Figure 1A:
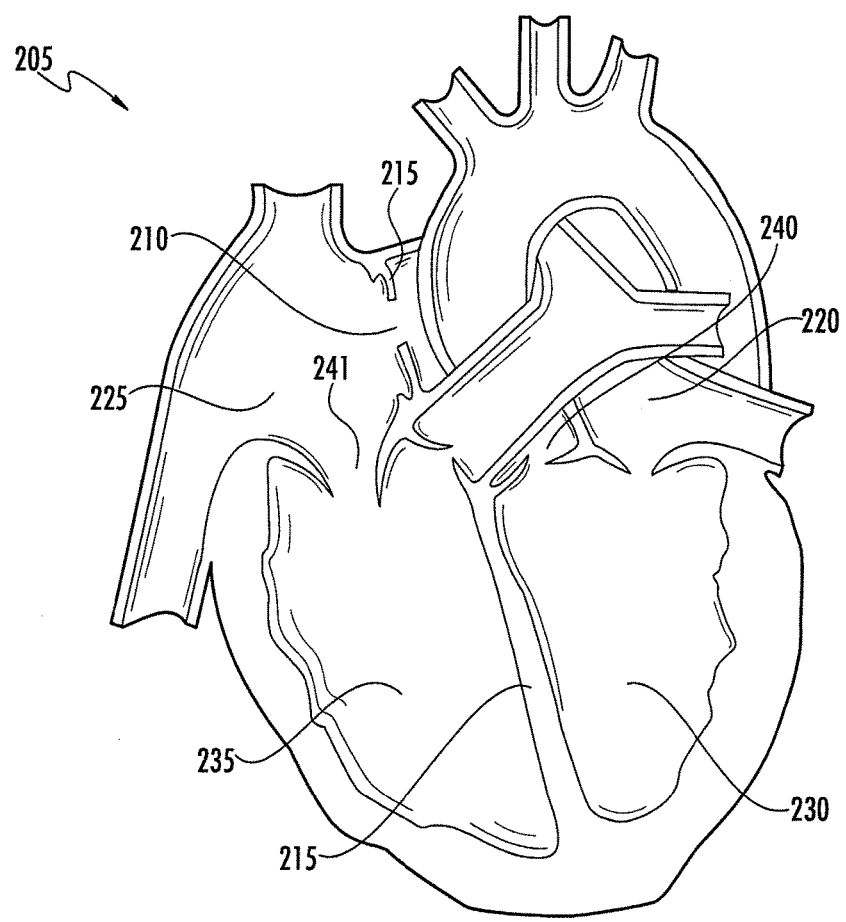
FIG. 1A is an illustration of an atrial septal defect.

Embodiments of the present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Embodiments provide a device for delivering a vascular device to a target site within a body lumen. As described in greater detail below, the vascular device may be, for example, a non-symmetric occluding device configured to occlude an abnormal opening in a patient's vasculature, such as a septal defect. In this regard, the vascular device may be geometrically non-symmetric (e.g., the shape of the vascular device may be non-symmetric about an axis of the vascular device), or the vascular device may be non-symmetric with respect to other properties (e.g., the materials used to make the vascular device, the distribution of weight or density, the distribution of a coating applied to the vascular device, etc.).

The vascular device may have a contracted state for allowing the vascular device to be received within a delivery sheath that has been positioned in a body lumen for deployment to the target site. The vascular device may also have an expanded state that is achieved when the vascular device is deployed from the delivery sheath, as described in greater detail below. For example, the vascular device may have a predetermined shape and may be collapsed by longitudinally stretching and inserting the vascular device into the lumen of the delivery sheath to constrain the vascular device in the contracted state. The delivery device with the attached vascular device may then be advanced through the delivery sheath to position the vascular device in a patient's body proximate the target site.

As the vascular device is advanced through the delivery sheath and out the distal end of the delivery sheath via distal movement of the delivery device with respect to the delivery sheath, the vascular device may substantially return to its expanded state. The delivery device and delivery sheath may then be removed from the patient's body, leaving the vascular device positioned at the target site.

It is understood that the use of the term "target site" is not meant to be limiting, as the vascular device may be configured to treat any target site, such as an abnormality, a vessel, an organ, an opening, a chamber, a channel, a hole, a cavity, or the like, located anywhere in the body. In the case of an occluding device, for example, the target site may be an abnormal opening in the patient's body, referred to herein as a "septal defect." A septal defect may be an abnormal or otherwise undesirable opening in a blood vessel, an organ, or other body tissues.

An example of a non-symmetric vascular device 10 that may be used for occluding a septal defect is shown in FIGS. 2A and 2B and is described more fully in the co-pending application titled Device and Method for Occluding a Septal Defect, filed concurrently herewith, the contents of which are incorporated by reference herein. For purposes of explaining the structure and function of embodiments of the delivery device, the example of a device 10 for occluding septal defects configured as shown in FIGS. 2A and 2B is used herein; however, it is understood that embodiments of the delivery device may be configured for use with various kinds of vascular devices that are used in different intravascular procedures, such as closure of para-valvular leaks, saccular aneurysms, and treatment of vessels that are other than circular in cross-section, among other procedures.

When positioning a vascular device that is not symmetric with respect to a longitudinal axis X of the vascular device within a body lumen, such as the vascular device 10 of FIGS. 2A and 2B, it is generally important to achieve the correct linear position (e.g., the position of the vascular device along the axis X) as well as the correct angular position (e.g., the rotational orientation of the vascular device in the direction R with respect to the axis X). For example, in the case of a vascular device 10 with an ovaloid portion 12 (e.g., as opposed to two circular portions), as depicted, the orientation of the major axis M of the ovaloid at the site of the defect may be important to avoid internal structures proximate the defect. Thus, as the user is positioning the vascular device 10 at the target site (e.g., at the septal defect), it may be necessary to rotate the vascular device within the body lumen to achieve the desired alignment of the major axis M.

Accordingly, a delivery device according to one embodiment is provided that is configured to be attached to a vascular device and to interface with other delivery tools and accessories so as to intravascularly deliver the vascular device to the target site, rotate the vascular device with respect to the target site and surrounding tissue to an appropriate orientation, release the vascular device once the vascular device is properly positioned, and be withdrawn from the body lumen, leaving the vascular device in place.

Referring now to FIG. 3, in general, the delivery device 20 may include an outer tubular member 30, an intermediate tubular member 40 at least partially disposed within the outer tubular member, and an inner member 50 at least partially disposed within the intermediate tubular member. The outer tubular member 30 may define a proximal end 32 and a distal end 34; the intermediate tubular member 40 may define a proximal end 42 and a distal end 44; and the inner member 50 may define a proximal end 52 and a distal end 54. As used herein, the term "proximal" refers to a part of the delivery device 20 that is closest to the operator (e.g., the surgeon or interventionalist) when the device is being delivered through the delivery device, and the term "distal" refers to a part of the delivery device that is farther from the operator.

The distal end 54 of the inner member 50 may be configured to engage a vascular device 10, such as the vascular device depicted in FIGS. 2A and 2B. For example, the distal end 54 of the inner member 50 may define external threads 56, and the external threads may be configured to engage corresponding internal threads defined in a bore 16 formed at a proximal end 14 of the vascular device 10 (shown in FIGS. 2A and 8B).

The inner member 50 may be configured to move axially through a lumen defined by the intermediate tubular member 40. In this regard, the inner member 50 may be, for example, a metallic wire or a strand or strands of another material having adequate stiffness to resist buckling when pushed and pulled through the intermediate tubular member 40, for example, to advance and/or retract an attached vascular device. The inner member 50 may also have adequate torsional rigidity to allow the distal end 54 of the inner member to be threaded to and unthreaded from the vascular device, as described below.

In some cases, as depicted in FIG. 3, the outer tubular member 30 may define a first length, and the intermediate tubular member 40 may define a second length. The first length may be shorter than the second length. In addition, the inner member 50 may define a third length, and the second length may be shorter than the third length. As a result, a user may be able to move the inner member 50 axially through the intermediate tubular member 40, for example, by pulling or pushing on a portion of the inner member proximate the proximal end 52 of the inner member, as described in greater detail below.

Figure 4:
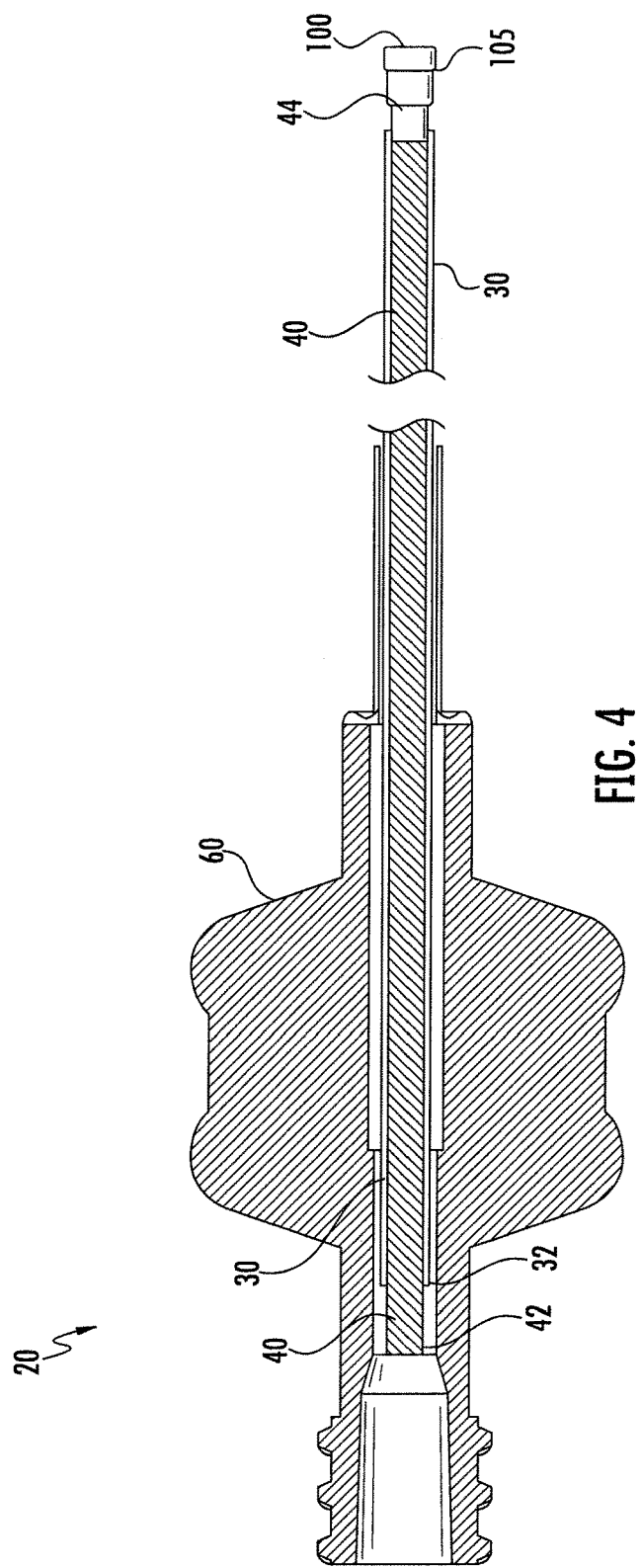
FIG. 4 is a partial cross-sectional view of a delivery device according to an exemplary embodiment.
Figure 5:
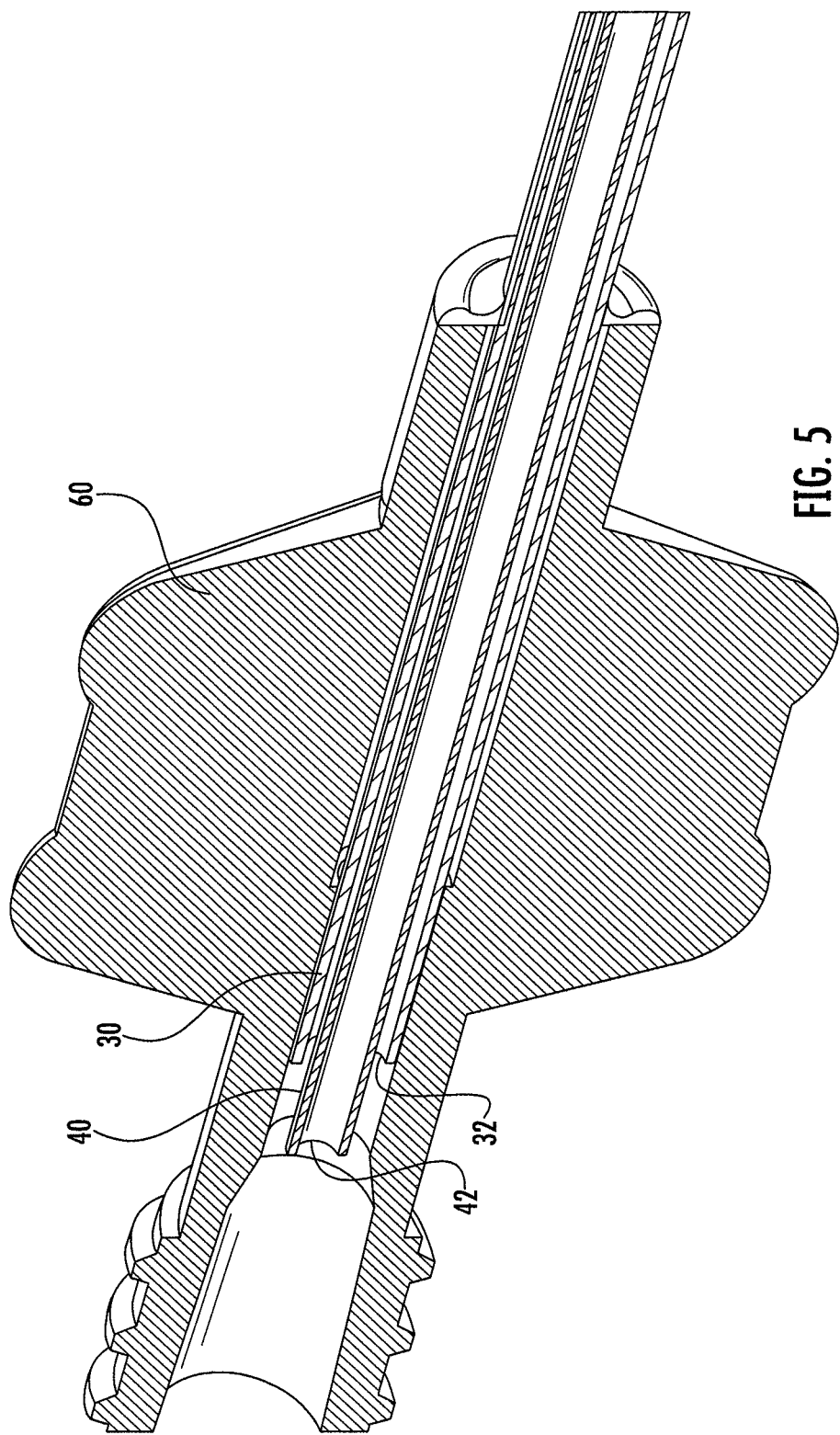
FIG. 5 is a perspective cross-sectional view of a hub of the delivery device of FIG. 3 according to an exemplary embodiment.

The proximal end 32 of the outer tubular member 30 may be fixed to the proximal end 42 of the intermediate tubular member 40. For example, the proximal ends 32, 42 of the outer and intermediate tubular members 30, 40 may be bonded, adhered, or otherwise affixed to each other at a hub 60. The hub 60 may be an overmolded plastic component, as shown in FIGS. 3, 4, and 5 and described in further detail below, or the hub may simply be a joint or connection point between the outer and intermediate tubular members 30, 40 made by using adhesives, welding, or other well known methods.

At the same time, the distal end 44 of the intermediate tubular member 40 may be free to rotate with respect to the distal end 34 of the outer tubular member 30. In other words, the distal ends 34, 44 of the outer and intermediate tubular members 30, 40 may be separate from each other (i.e., not fixed), with a clearance defined therebetween. The clearance may be, for example, a distance roughly equivalent to the wall thickness of the intermediate tubular member 40. In this way, a torque applied to the hub 60 and thereby applied to the proximal end 32 of the outer tubular member 30 and the proximal end 42 of the intermediate tubular member 40 (e.g., via the hub 60) may be at least partially, and in many cases substantially, transmitted to the distal end 44 of the intermediate tubular member. For example, for an applied torque resulting from the rotation of the hub 60 in either the clockwise or counter clockwise direction of approximately 180°, the rotational displacement of the distal end 44 of the intermediate tubular member 40 may be in the range of approximately 120° to approximately 230° and is typically approximately 160° to approximately 174° (in the same direction as the applied torque).

Stated differently, there may be frictional resistance between an outer surface of the outer tubular member 30 and an inner surface of a delivery sheath (described below) within which the delivery device 20 is moved. Furthermore, the outer tubular member 30 may have a low torsional rigidity due to the use of polymeric material to make the outer tubular member, such that when torque is applied to a proximal end 32 of the outer tubular member (e.g., via the hub 60), a rotational displacement of the hub may result in little rotation of the distal end 34 of the outer tubular member. Because the outer tubular member 30 is not connected to the intermediate tubular member 40 at the respective distal ends 34, 44, this lack of rotational displacement at the distal end 34 of the outer tubular member does not substantially impede the rotational displacement at the distal end 44 of the intermediate tubular member 40, thereby improving the torque response and rotational control of the attached vascular device 10 as compared to a conventional delivery system.

For example, when tested under a standard test protocol wherein the delivery system is placed through a delivery sheath having a preset 90° bend near its distal end, an input 180° rotation of the hub 60 (in both the clockwise and counterclockwise direction) resulted in an average angular displacement of the distal end 44 of the intermediate tubular member 40 in the same direction of approximately 160° to 174°. In comparison, conventional delivery systems typically measure 0° of rotation in either direction at the distal end (in either direct) for the same 180° input at the hub 60.

Figure 6:
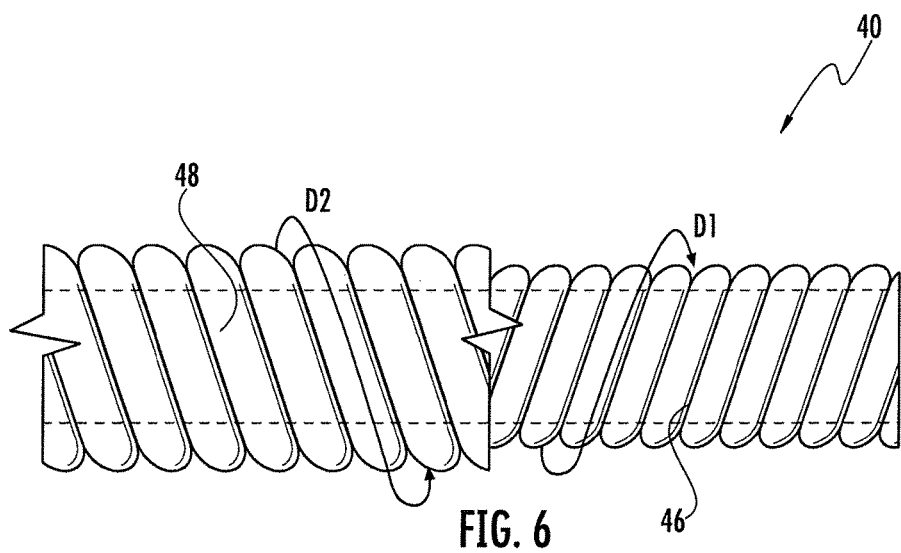
FIG. 6 is a schematic illustration of first and second filaments of an intermediate tubular member of the delivery device according to an exemplary embodiment.

Thus, in some embodiments, the intermediate tubular member 40 is configured to transmit torque from one end to the other. For example, as depicted in FIG. 4, which shows a partial cross-section of the delivery device 20, and FIG. 6, the intermediate tubular member 40 may comprise at least two filaments that are spirally wound in alternating directions. In the case of two spirally wound filaments, with reference to FIG. 6, a first filament 46 may be spirally wound in a first direction D1 and may form an inner layer of the intermediate tubular member 40. A second filament 48 may be spirally wound on top of the first filament 46 to form an outer layer, but in a second direction D2 that is different from the first direction D1. For example, the first filament 46 may be a left-hand wind, whereas the second filament 48 may be a right-hand wind.

In this way, a torque applied to one end of the intermediate tubular member 40 in the first direction D1, although having the tendency to loosen the winding of the first filament 46, is prevented from doing so by the inner diameter of the second filament 48, thus allowing the transmission of torque. Similarly, a torque applied to one end of the intermediate tubular member 40 in the second direction D2, although having the tendency to tighten the winding of the second filament 48, is prevented from doing so by the outer diameter of the first filament 46, again allowing the transmission of torque from one end to the other. In other words, the opposing reactions by the first and second filaments 46, 48 serve to transmit the torque from the one end of the intermediate tubular member 40 to the other end for rotation in either direction.

As noted above, in some cases more than two filaments may be used. For example, three filaments may be spirally wound in alternating directions to form the intermediate tubular member 40. Again, because the filaments are wound in alternating directions, a torque applied at one end of the intermediate tubular member 40 would be at least partially transmitted to the other end. In addition, a material that is rigid and capable of transmitting an applied torque, such as a metal (e.g., stainless steel), may be used to make the filaments 46, 48.

In some embodiments, substantially all of an applied torque is transmitted to the distal end of the intermediate tubular member 40. For example, in the case of three metallic filaments that are spirally wound in alternating directions, approximately 66% to approximately 95% of the angular displacement input (180° rotation) applied to the hub 60 is transmitted to the distal end 44 of the intermediate tubular member 40 as angular displacement output, and, in one embodiment, at least 25% of the torque is transmitted to the distal end.

Referring again to FIGS. 4 and 5, the spirally wound filaments 46, 48 forming the intermediate tubular member 40 may be fixed at their proximal ends 42 to the proximal end 32 of the outer tubular member 30 and, in some cases, to the hub 60 through an over molding process. For example, in some embodiments, the outer tubular member 30 may be made of a polymeric material, such as nylon, and may be melted onto the spirally wound filaments 46, 48 of the intermediate tubular member 40 at the respective proximal ends 32, 42. The filaments 46, 48 may be bonded to each other at the distal end 44 to prevent relative motion between them. The hub 60 may in turn be fused to the outer tubular member 30 and the intermediate tubular member 40. In this regard, a piece of heat shrink may be placed over the outer tubular member 30 such that the heat shrink is over both the outer tubular member and the outer layer of the spirally wound filaments. As the assembly is heated, the heat shrink is also heated and shrinks onto the nylon outer tubular member 30. The heat shrink, in turn, may shrink the nylon material of the outer tubular member 30 onto the spirally wound coil. Accordingly, the hub 60 may be applied to the outer tubular member 30 via a compression fit and, potentially, additional reflow of the polymer tubing onto the metallic filaments.

Figure 11A:
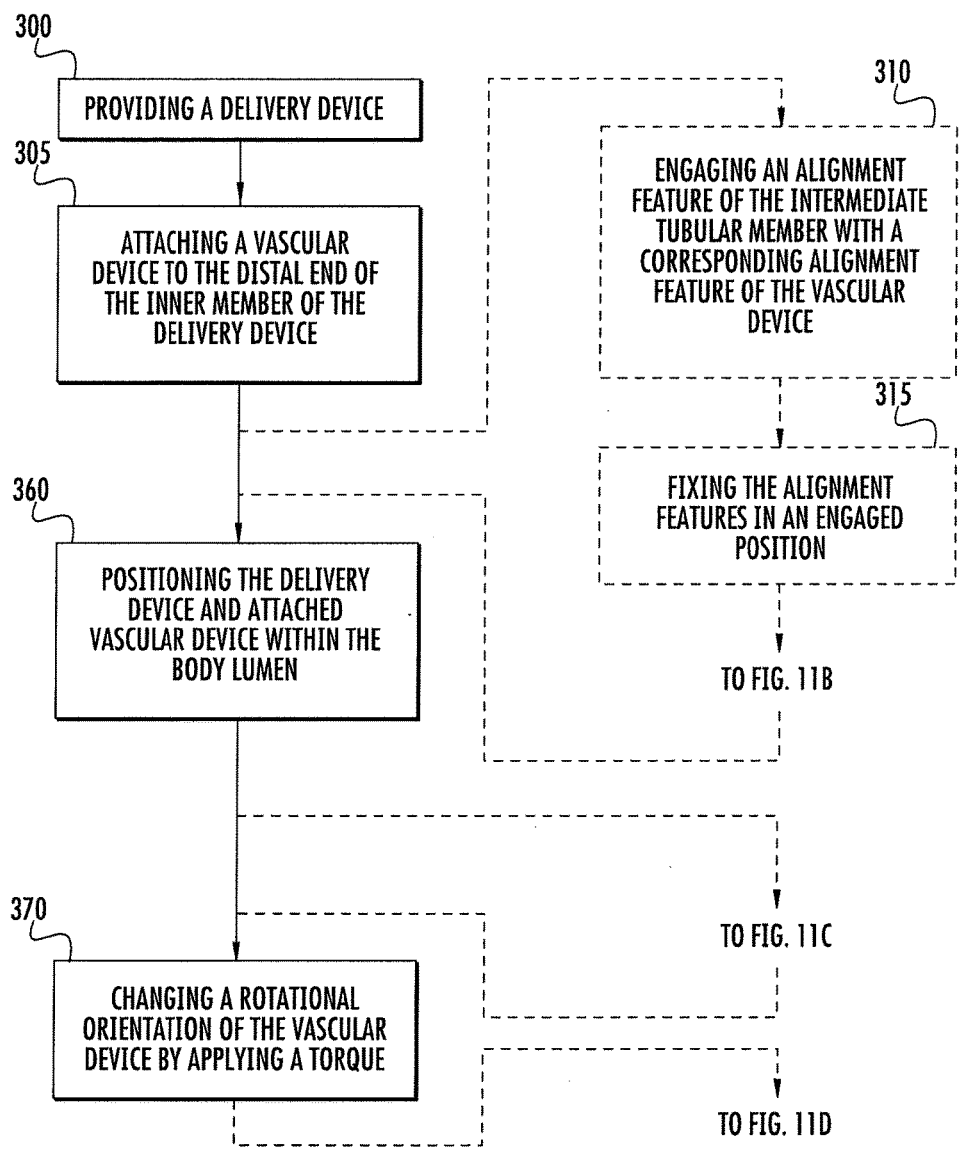

FIGS. 11A-11D depict embodiments of a method for orienting a vascular device, such as a non-symmetric vascular device, within a body lumen and are referenced below. As noted above and illustrated in FIGS. 2A and 7, a distal end 54 of the inner member 50 may be configured to releasably attach to the vascular device 10. FIG. 11A, Block 300, 305. For example, the vascular device 10 may include an end feature 18 at its proximal end 14 that is configured to receive the distal end 54 of the inner member 50. In the depicted embodiment, the end feature 18 defines a threaded bore 16 (shown in FIG. 8B) that is configured to receive and engage the threaded 56 distal end 54 of the inner member 50.

With additional reference to FIGS. 8A and 8B, in some embodiments, the intermediate tubular member 40 comprises an alignment feature 100 at the distal end 44 of the intermediate tubular member that is configured to engage a corresponding alignment feature 110 defined, for example, by the end feature 18 of the vascular device 10. The alignment features 100, 110 may be configured such that, when engaged, a rotation of the distal end 44 of the intermediate tubular member 40 results in a corresponding rotation of the vascular device 10. In other words, the distal end 44 of the intermediate tubular member 40 may be rotationally fixed to the vascular device 10 when the alignment features 100, 110 are engaged. In some cases, for example as shown in FIGS. 8A and 8B, the alignment feature 100 of the intermediate tubular member 40 may comprise a D-shaped coupling 105 that is configured to engage a corresponding D-shape defined by the end feature 18 of the vascular device 10 (e.g., via corresponding notches, as shown). As shown in FIGS. 4 and 9, the D-shaped coupling 105 of the delivery device 20 defining the alignment feature 100 may be attached to the intermediate tubular member 40 directly through any suitable method, such as by welding, adhering, or otherwise fixing the coupling 105 to the distal end 44 of the intermediate tubular member (e.g., by attaching to the first and/or second filaments 46, 48 that are spirally wound to form the intermediate tubular member). FIG. 11A, Block 310.

Turning again to FIG. 3, the delivery device 20 may further comprise a handle 120 that is selectively fixed to the proximal end 32 of the outer member 30. The handle 120 may be used to maintain engagement of the alignment features 100, 110 of the delivery device 20 and the vascular device 10, respectively, such that, as the user is positioning the delivery device and the attached vascular device within the body lumen, the orientation of the vascular device can be controlled by the user at a distal end of the delivery device, as described below.

Figure 12:
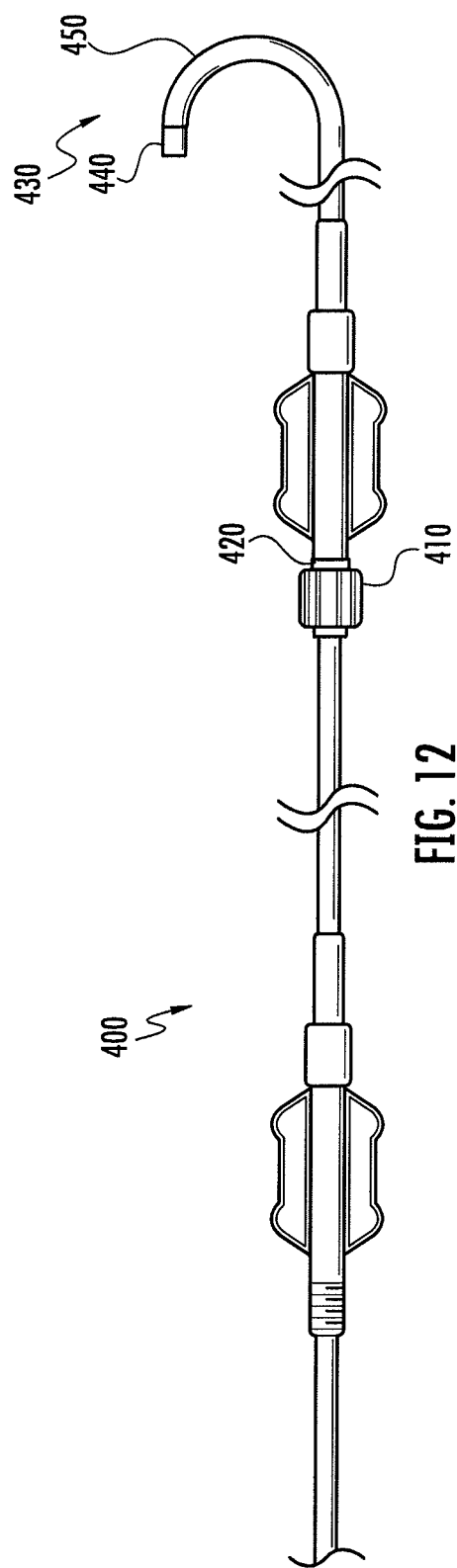
FIG. 12 illustrates a device introducer and a delivery sheath that may be used with the delivery device according to an exemplary embodiment.

The delivery device 20 may be configured to be used with other delivery instruments and accessories designed to facilitate draw-down of the vascular device 10 to a contracted state for insertion into a delivery sheath 430 (shown in FIG. 12 having a curved distal portion). For example, with regard to a self-expanding vascular device 10 configured to have a contracted state when constrained and an expanded stated when unconstrained, the delivery device 20 may be configured to be back-loaded into a device introducer 400 (shown in FIG. 12) that is designed to radially constrain the vascular device from the expanded state to the contracted state. The device introducer 400 may, for example, be configured to be attached at its distal end 410 by a luer connector to the proximal end 420 of the delivery sheath 430. The operator may position the inner member 50 through the delivery device 20 lumen with the threaded portion 54 extending past the distal ends 34,44 of the outer and intermediate tubular members 30, 40. The delivery device 20 may be passed through the proximal end of the device introducer 400 lumen such that the distal ends 34,44 extend past the distal end of the device introducer.

The axial position of the handle 120 may be adjusted along the inner member 50 (e.g., in the directions indicated by the arrow A) by the user through manipulation of an engagement device, such as a locking knob 125, which is configured to engage the inner member within a lumen of the handle when the knob is tightened, thereby locking the handle to the inner member. For example, when preparing the delivery device 20 for an intravascular procedure, the user may initially attach the vascular device 10 to the distal end 54 of the inner member 50 via the threads 56, as illustrated in FIG. 7. The user may then engage the alignment features 100, 110 by moving the proximal end 52 of the inner member 50 proximally until the D-shaped coupling 105 (FIGS. 4 and 7) contacts the end feature 18 of the vascular device 10 (for example, by fixing the handle 120 to the inner member via the knob 125 and pulling on the handle to move the inner member proximally). At that point, the user may rotate the handle 120, thereby rotating the inner member 50 and the attached D-shaped coupling 105 until the alignment features 100, 110 are matched up and engage each other. The user may, for example, determine whether engagement has occurred by continuing to pull gently on the inner member 50 in the proximal direction as the handle 120 is rotated and feeling a perceptible identification (e.g., a snap) as the alignment features 100, 110 are engaged.

Once the alignment features 100, 110 are engaged, the user may loosen the knob 125 of the handle 120 and slide the handle along the inner member 50 distally until the handle is proximate to and/or contacts the hub 60 and cannot be moved further in the distal direction. At that point, the knob 125 may be tightened again to lock the handle 120 in this position along the inner member 50. In so doing, the alignment features 100, 110 are locked in the engaged state, as the inner member 50 can no longer be moved with respect to the intermediate tubular member 40, being locked at the distal end by the handle 120 and at the proximal end by the end feature 18 and the vascular device 10 itself. FIG. 11A, Block 315.

Figure 11B:
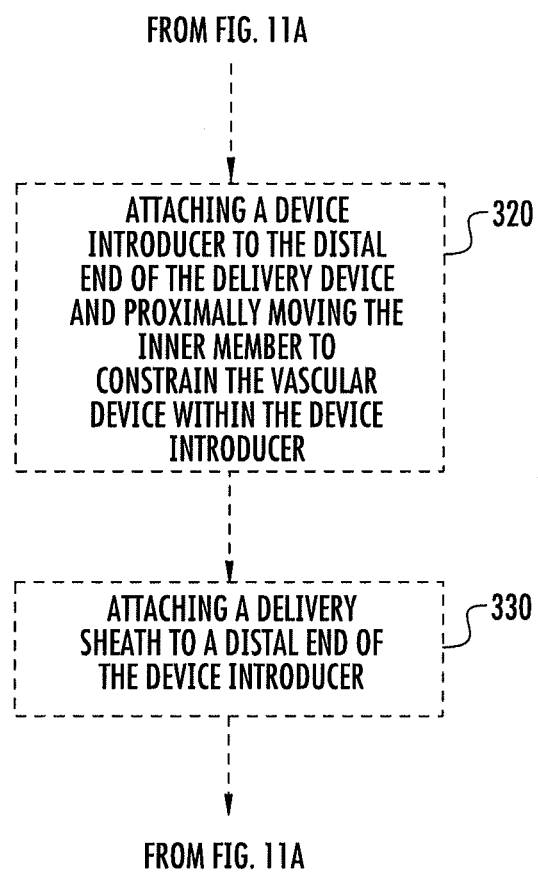

As noted above, once the vascular device 10 is attached to the inner member 50 (distally of the device introducer) and the alignment features 100, 110 are engaged and locked, the user may draw the delivery device in a distal direction by holding the device introducer 400 in place and drawing the delivery device 20 proximally until the device is fully contained within the lumen of the device introducer (e.g., via the hub 60). FIG. 11B, Block 320. The configuration of the device introducer 400 is such that the vascular device 10 is radially constrained from the expanded state to the contracted state as it is moved proximally through the device introducer, the lumen of the device introducer having a diameter no larger (and preferably smaller) than the lumen of the delivery sheath 430 to facilitate passage into the sheath without damage to the vascular device.

Figure 11C:
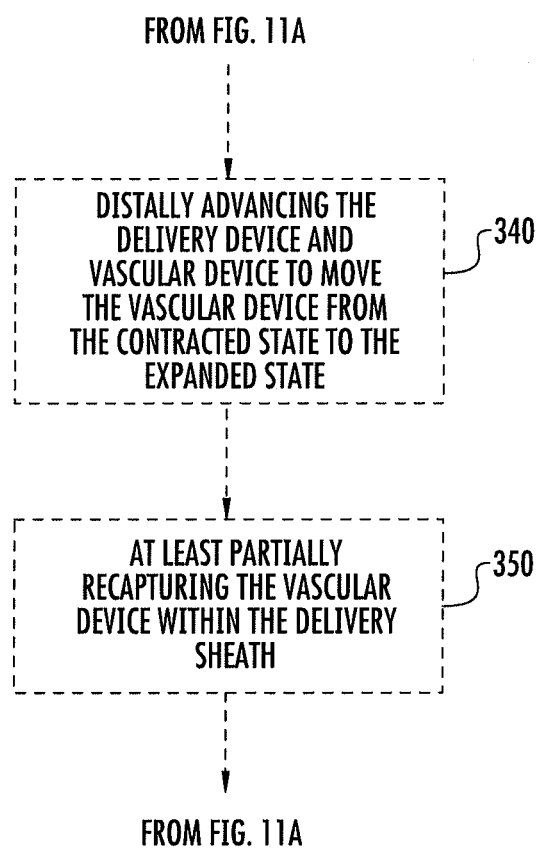

Referring to FIG. 12, when the vascular device 10 has achieved a contracted state within the device introducer, a distal end 410 of the device introducer 400 may be attached to a proximal end 420 of a delivery sheath 430, as will also be understood by those skilled in the art in light of this disclosure. FIG. 11B, Block 330. The vascular device 10 and at least a distal portion of the delivery system 20 (e.g., a portion of the delivery system distal of the hub 60) may be configured to be moved axially through the delivery sheath 430, which may already be positioned within the body lumen to facilitate positioning of the delivery device within the body lumen. In this way, the delivery device 20 and the attached vascular device 10 may be advanced through the delivery sheath 430 to move the vascular device from the contracted state to the expanded state (i.e., once the vascular device is advanced distally of the distal end 440 of the delivery sheath and is, thus, no longer constrained by the delivery sheath). FIG. 11C, Block 340.

In some cases, it may be necessary to at least partially recapture the vascular device 10 within the delivery sheath 430 by retracting the delivery device 20 and the attached vascular device back through the distal end 440 of the delivery sheath. FIG. 11C, Block 350. This may be necessary, for example, when positioning a vascular device within a septal defect, in which case a distal end of the vascular device may need to be expanded, while a proximal end of the vascular device may need to be contracted to allow the user to position the vascular device across the defect, as will be understood by those skilled in the art in light of this disclosure.

Figure 1B:
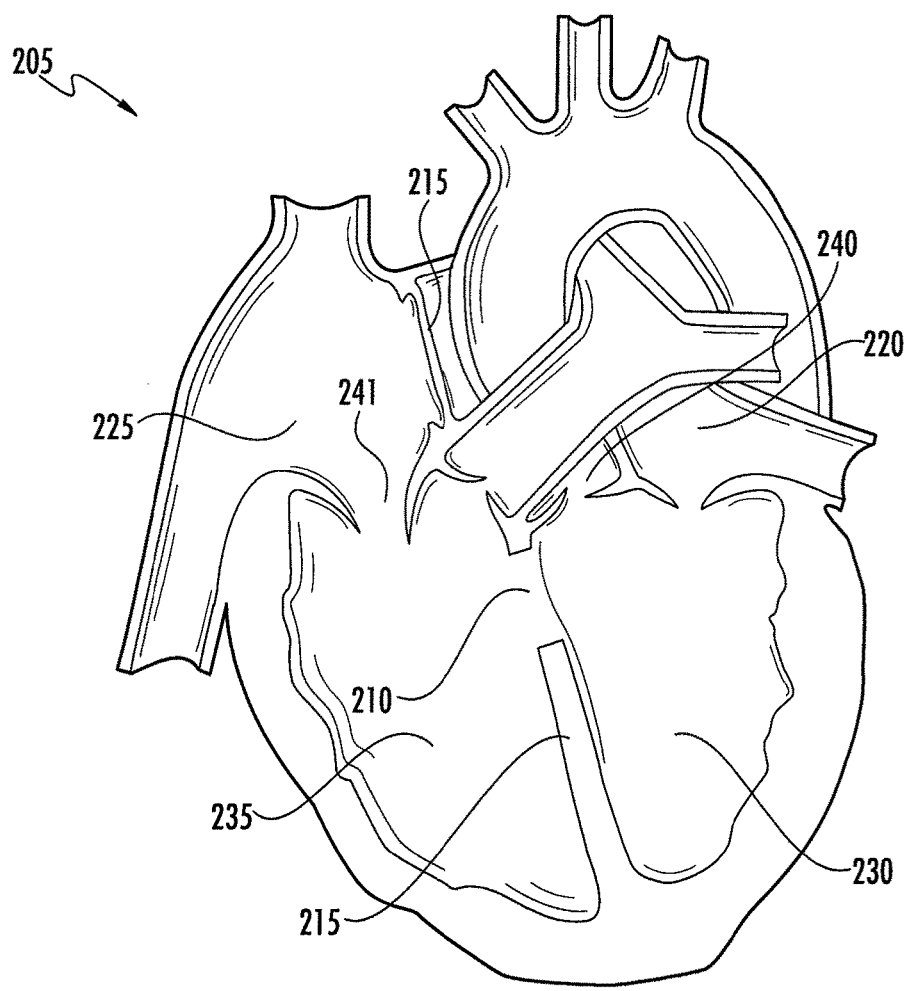
FIG. 1B is an illustration of a ventricular septal defect.

More particularly, when occluding a septal defect, for example, the vascular device may be allowed to self-expand to its expanded state distally of the septal defect. Referring to FIG. 1B, the delivery device and the attached vascular device may be positioned within the body lumen (FIG. 11A, Block 360) by, for example, inserting the delivery device via the delivery sheath through the inferior vena cava, into the right atrium 225, through the tricuspid valve 241, into the right ventricle 235, across the ventricular septal defect 210, and into the left ventricle 230, where the vascular device may be deployed from the delivery sheath and allowed to self-expand. At that point, the medical practitioner may change a rotational orientation of the vascular device as desired, for example, by applying a torque to the proximal end of the intermediate tubular member 40 (e.g., via the hub 60). FIG. 11A, Block 370. Because the outer tubular member 30 and the intermediate tubular member 40 are fixed to each other at their respective proximal ends 32, 42 but are not fixed at their distal ends 34, 44 (FIGS. 3 and 4), the torque applied at the proximal ends may be at least partially transmitted to the distal end of the intermediate tubular member and may serve to change the rotational orientation of the vascular device that is rotationally attached to the intermediate tubular member via the respective alignment features 100, 110. Thus, by observing radiopaque images of the delivery device 20 and/or the vascular device 10, the user may determine when the vascular device is in the appropriate position, both axially and rotationally. Accordingly, the vascular device and/or the delivery device may include at least one radiopaque marker that is observable to the user via fluoroscopy techniques.

Once the vascular device 10 is in the desired orientation, the delivery sheath may be held in position while the delivery device 20 (with the vascular device 10 still attached) is partially retracted back into the delivery sheath, for example, such that only proximal parts of the vascular device is moved back to the contracted state within the delivery sheath. The delivery device 20 and delivery sheath may then be retracted together proximally, such that the distal portion 12 of the vascular device (which is still in the expanded state) may be moved into engagement with the corresponding septal wall surface. With the distal portion 12 in place, the delivery device 20 may be held in position while the delivery sheath is again retracted proximally to deploy the remaining portions of the vascular device, thereby allowing the remaining portions to self-expand and engage the central defect and opposite side of the septal wall and installing the vascular device across the septal defect.

When the vascular device has been appropriately positioned by the user, the vascular device may be detached from the distal end of the inner member 50, and the alignment feature 100 of the intermediate tubular member 40 may be disengaged from the alignment feature 110 of the vascular device 10. FIG. 11D, Block 380. For example, referring to FIGS. 3 and 7, with the alignment features 100, 110 still attached, the proximal end 52 of the inner member 50 may be rotated to unthread the distal end 54 from the vascular device 10. With the inner member 50 detached from the vascular device 10, the delivery device 20 may be retracted proximally to disengage the D-shaped coupling 105 from the end feature 18 of the vascular device, thereby withdrawing the delivery device (and the delivery sheath) from the body lumen and leaving the vascular device installed at the target site. FIG. 11D, Block 390.

Figure 10:
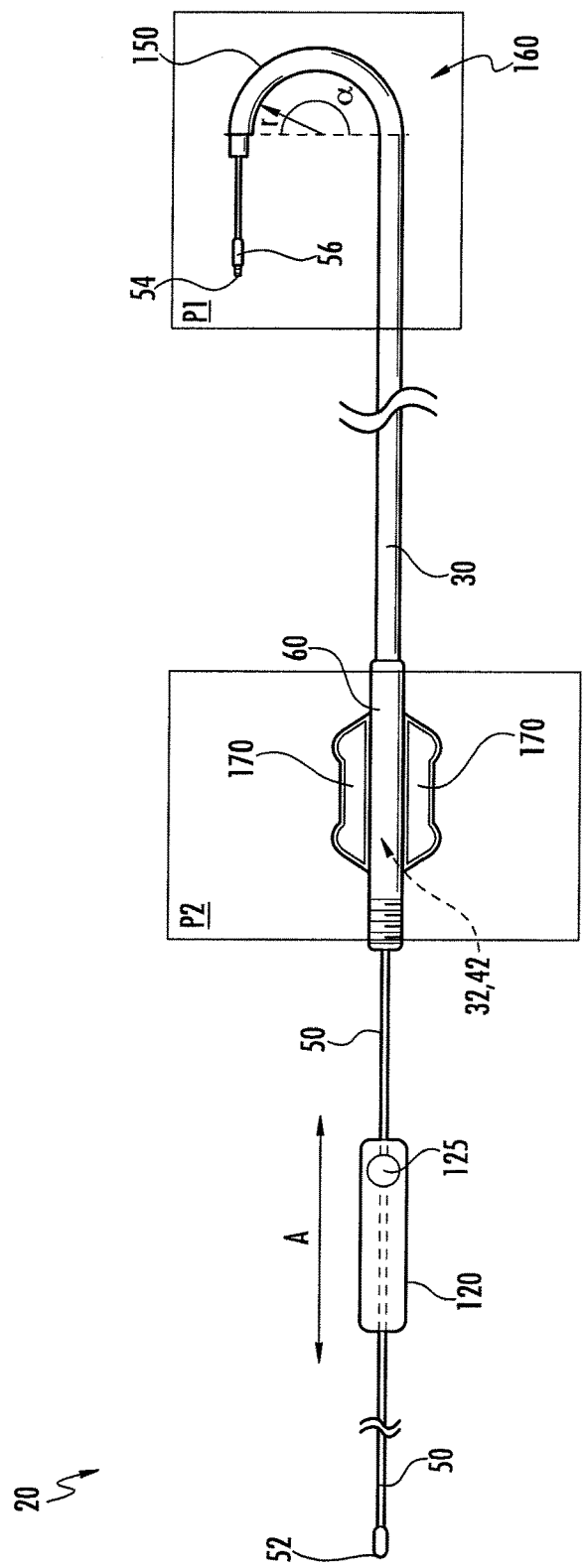
FIG. 10 is a schematic illustration of a delivery device with a prebend according to an exemplary embodiment.

With reference to FIG. 10, in some embodiments, the outer tubular member 30 may define a prebend 150 in a distal portion 160 of the outer tubular member. The prebend 150 may be configured to facilitate insertion of the delivery device through the body lumen. In this regard, a distal portion of the delivery sheath 430, through which the delivery device 20 is advanced as described above, may define a corresponding prebend 450, and thus the prebend 150 of the delivery device may allow the delivery device to be more easily advanced through the delivery sheath to the target site.

The outer tubular member 30 may be heat formed to include the prebend 150, or the prebend may be defined in the outer tubular member through heat treatment or other processing of the outer tubular member to achieve and maintain a bend having a predetermined radius of curvature, as will be recognized by those skilled in the art in light of this disclosure. In some embodiments, the prebend 150 has a curvature that is configured to match the natural curvature in a particular portion of the patient's vasculature, such as the vasculature in the area of the target site. In this way, the delivery device 20, by virtue of the prebend 150, may more easily and more comfortably be advanced to the target site, as will be recognized by those skilled in the art in light of this disclosure. For example, when treating an atrial or ventricular septal defect, the prebend 150 may be configured to have a radius of curvature r of between approximately 0.5 inches and approximately 3 inches and an angle α of between approximately 150° and approximately 210°. In the embodiment depicted in FIG. 10, for example, the prebend 150 has a radius of curvature r of approximately 1.5 inches and an angle α of approximately 180° (i.e., the distal end 34 of the outer tubular member 30 is pointing in a direction that is approximately 180° from the path of the linear portion of the outer tubular member).

In some cases, the delivery device 20 includes a curve alignment feature that allows the user to align the prebend 150 with the proximal end 32 of the outer tubular member 30. Referring to FIG. 10, for example, the hub 60 may include one or more wings 170 that are pre-configured in relationship to the prebend 150 with the proximal end of the outer tubular member 30. For example, the prebend 150 may lie substantially within a first plane P1, and the wing(s) 170 may define a second plane P2 that is substantially parallel to the first plane P1, as shown. The delivery sheath 430 (shown in FIG. 12) may have a similar pre-bend 450 and curve alignment feature as the delivery device 20. Thus, when first inserting the delivery device 20 into the delivery sheath 430, it may be useful for the operator to align the respective pre-bends 450, 150 by aligning the wings of the respective devices.

FIGS. 11A-11D, discussed above, present a flowchart of a method for orienting a vascular device within a body lumen according to example embodiments of the delivery device. Dashed lines and boxes indicate optional steps of the method. Additionally, although the steps are presented in a particular order in FIGS. 11A-11D, some of the steps may be performed in an order other than what is presented in the figures or may occur substantially simultaneously with other steps according to the particular vascular device being used, the intravascular procedure being conducted, the configuration of the delivery device, and user preferences.

This invention has been described herein in considerable detail in order to comply with the Patent Statutes and to provide those skilled in the art with the information needed to apply the novel principles and to construct and use embodiments of the example as required. However, it is to be understood that specifically different devices can carry out the invention and that various modifications can be accomplished without departing from the scope of the invention itself. For example, options shown for one embodiment could easily be applied to other embodiments, as desired for a particular application, without departing from the scope of this invention.

That which is claimed:

1. A device for delivering a vascular device within a body lumen via a delivery sheath, the delivery device comprising:
    an outer tubular member having a proximal end and a distal end;
    an intermediate tubular member at least partially disposed within the outer tubular member, the intermediate tubular member having a proximal end and a distal end, the distal end of the intermediate member configured to engage the vascular device; and
    an inner member at least partially disposed within the intermediate tubular member and movable axially therein, the inner member having a proximal end and a distal end, the distal end of the inner member defining threads configured to engage corresponding threads on a proximal end of the vascular device;
    wherein the proximal end of the outer tubular member and the proximal end of the intermediate tubular member are fixed to each other, the distalmost end of the intermediate tubular member and the distal end of the outer tubular member having a clearance defined between an inner surface of the outer tubular member and an outer surface of the intermediate tubular member, the delivery device configured such that a torque applied proximate the proximal end of the outer tubular member is at least partially transmitted to the distal end of the intermediate tubular member to adjust a rotated position of the vascular device and a rotated position of the distal end of the intermediate tubular member relative to the outer tubular member due to a frictional resistance of the outer tubular member with respect to the delivery sheath through which the delivery device is moved during delivery of the vascular device.

2. The delivery device of claim 1, wherein the outer tubular member defines a first length, the intermediate tubular member defines a second length, and the inner member defines a third length, and wherein the first length is shorter than the second length and the second length is shorter than the third length.

3. The delivery device of claim 1, wherein the intermediate tubular member comprises an alignment feature at the distal end thereof configured to engage a corresponding alignment feature of the vascular device such that a rotation of the distal end of the intermediate tubular member results in a corresponding rotation of the vascular device.

4. The delivery device of claim 3, wherein the alignment feature comprises a D-shaped coupling.

5. The delivery device of claim 3 further comprising a handle that is selectively fixed to the proximal end of the inner member, wherein the axial position of the handle along the inner member is adjustable, and wherein fixation of the handle to the inner member maintains engagement of the alignment features.

6. The delivery device of claim 1, wherein the outer tubular member defines a prebend in a distal portion thereof to facilitate insertion of the delivery device through the body lumen.

7. The delivery device of claim 6, wherein the prebend has a curvature of between approximately 150° and approximately 210°.

8. The delivery device of claim 6 further comprising a hub at which the proximal end of the outer tubular member and the proximal end of the intermediate tubular member are fixed to each other, wherein the hub comprises at least one wing to facilitate alignment of the prebend with a prebend of the delivery sheath through which the delivery device is moved.

9. The delivery device of claim 8, wherein the prebend lies substantially within a first plane, and wherein the at least one wing defines a second plane that is substantially parallel to the first plane.

10. The delivery device of claim 1, wherein the intermediate tubular member comprises a plurality of spirally wound filaments.

11. The delivery device of claim 10, wherein the intermediate tubular member comprises at least two metallic filaments spirally wound in alternating directions.

12. The delivery device of claim 10, wherein the intermediate tubular member comprises three metallic filaments spirally wound in alternating directions.

13. The delivery device of claim 1, wherein the delivery device is configured to pass through a device introducer, wherein the device introducer radially constrains the vascular device from an expanded state to a contracted state.

14. The delivery device of claim 13, wherein a distal end of the device introducer is configured to be attached to a proximal end of the delivery sheath, and wherein the vascular device and at least a distal portion of the delivery device are movable axially through the delivery sheath for positioning the vascular device proximate a target site within the body lumen.

15. A device for deploying a vascular device within a body lumen via a delivery sheath, the delivery device comprising:
an outer tubular member having a proximal end and a distal end;
an intermediate tubular member comprising at least a first filament and a second filament, wherein the first and second filaments are spirally wound in alternating directions and the second filament is wound over top of the first filament, the intermediate tubular member being at least partially disposed within the outer tubular member and having a proximal end and a distal end, the distal end of the intermediate member configured to engage the vascular device; and
an inner member at least partially disposed within the intermediate tubular member and movable axially therein, wherein the inner member defines a proximal end and a distal end, the distal end of the inner member defining threads configured to engage corresponding threads on a proximal end of the vascular device;
wherein the proximal end of the outer tubular member and the proximal end of the intermediate tubular member are fixed to each other, the distal end of the intermediate tubular member and the distal end of the outer tubular member having a clearance defined between an inner surface of the outer tubular member and an outer surface of the intermediate tubular member, the delivery device configured such that a torque applied proximate the proximal end of the outer tubular member is transmitted to the distal end of the intermediate tubular member and serves to rotate the vascular device and the distal end of the intermediate tubular member relative to the outer tubular member due to a frictional resistance of the outer tubular member with respect to the delivery sheath through which the delivery device is moved during delivery of the vascular device.

16. The delivery device of claim 15, wherein the intermediate tubular member comprises an alignment feature at the distal end thereof configured to engage a corresponding alignment feature of the vascular device such that a rotation of the distal end of the intermediate tubular member results in a corresponding rotation of the vascular device.

17. The delivery device of claim 16 further comprising a handle that is selectively fixed to the proximal end of the inner member, wherein the axial position of the handle along the inner member is adjustable, and wherein fixation of the handle to the inner member maintains engagement of the alignment features.

18. The delivery device of claim 15, wherein the outer tubular member defines a prebend in a distal portion thereof that facilitates insertion of the delivery device through the body lumen.

19. The delivery device of claim 15 further comprising a hub at which the proximal end of the outer tubular member and the proximal end of the intermediate tubular member are fixed to each other.

20. The delivery device of claim 15, wherein the intermediate tubular member comprises at least three filaments spirally wound in alternating directions.

21. A method for orienting a vascular device within a body lumen comprising:
providing a delivery device having a proximal end and a distal end, the delivery device comprising:
an outer tubular member;
an intermediate tubular member at least partially disposed within the outer tubular member, wherein a proximal end of the outer tubular member and a proximal end of the intermediate tubular member are fixed to each other, a distalmost end of the intermediate tubular member and a distal end of the outer tubular member having a clearance defined between an inner surface of the outer tubular member and an outer surface of the intermediate tubular member; and
an inner member at least partially disposed within the intermediate tubular member and movable axially therein,
engaging a proximal end of the vascular device with a distal end of the inner member;
engaging the vascular device with a distal end of the intermediate tubular member;
positioning the delivery device and the attached vascular device within a delivery sheath within the body lumen;
rotating the vascular device relative to the body lumen about a longitudinal axis of the delivery device with the intermediate tubular member by applying a torque to a proximal end of the outer tubular member such that the torque applied to the proximal end of the outer tubular member is transmitted to the distal end of the intermediate tubular member and serves to rotate the vascular device and the distal end of the intermediate tubular member relative to the outer tubular member due to a frictional resistance of the outer tubular member with respect to the delivery sheath; and
disconnecting the inner member from the vascular device to deposit the vascular device within the body lumen.

22. The method of claim 21 further comprising attaching a device introducer to the distal end of the delivery device and proximally retracting the inner member with respect to the device introducer to constrain the vascular device to a contracted state within the device introducer.

23. The method of claim 22 further comprising attaching the delivery sheath to a distal end of the device introducer to facilitate positioning of the delivery device within the body lumen.

24. The method of claim 23 further comprising distally advancing the delivery device and the vascular device through the device introducer and the delivery sheath to radially constrain the vascular device from the contracted state to an expanded state proximate a target site.

25. The method of claim 24 further comprising at least partially recapturing the vascular device within the delivery sheath.

26. The method of claim 21, wherein contacting the vascular device with the distal end of the intermediate tubular member comprises engaging an alignment feature disposed at the distal end of the intermediate tubular member with a corresponding alignment feature of the vascular device.

27. The method of claim 26, wherein the step of engaging the alignment feature comprises axially retracting the inner member in a proximal direction with respect to the intermediate tubular member.

28. The method of claim 27, wherein the step of engaging the alignment feature further comprises fixing the alignment features in an engaged position such that axial movement of the inner member with respect to the intermediate member is prevented.

29. The method of claim 27, further comprising disengaging the alignment feature of the intermediate tubular member from the corresponding alignment feature of the vascular device.

30. The method of claim 21, wherein disconnecting the inner member from the vascular device includes rotating the inner member relative to the vascular device.

31. The method of claim 21, further comprising the step of verifying an alignment of a prebend of the outer tubular member with respect to a prebend of the delivery sheath through which the delivery device is passed.

\* \* \* \* \*